(12) United States Patent
Quintin

(10) Patent No.: US 8,846,606 B2
(45) Date of Patent: Sep. 30, 2014

(54) METHOD AND DRUG COMPOSITION FOR TREATING SEPTIC SHOCK HYPOTENSION

(76) Inventor: Luc Quintin, Lyons (FR)

( * ) Notice: Subject to any disclaimer, the term of this patent is extended or adjusted under 35 U.S.C. 154(b) by 37 days.

(21) Appl. No.: 13/168,889

(22) Filed: Jun. 24, 2011

(65) Prior Publication Data

US 2011/0269666 A1    Nov. 3, 2011

(30) Foreign Application Priority Data

Apr. 30, 2010   (FR) ..................... 10 53355

(51) Int. Cl.
*A61K 45/06*      (2006.01)
*A61K 31/137*     (2006.01)
*A61K 31/4168*    (2006.01)

(52) U.S. Cl.
CPC ............. *A61K 45/06* (2013.01); *A61K 31/4168* (2013.01); *A61K 31/137* (2013.01)
USPC ............ 514/1.4; 514/334; 514/377; 514/396; 514/398; 514/567

(58) Field of Classification Search
CPC . A61K 31/137; A61K 31/4168; A61K 45/06; A61K 2300/00
USPC ................... 514/1.4, 334, 377, 396, 398, 567
See application file for complete search history.

(56) References Cited

PUBLICATIONS

Clonidine from MedlinePlus, pp. 1-4. Accessed Jan. 9, 2013.*
Moreau R, Cailmail S, Lebrec D, "Effects of vasopressin on haemodynamics in portal hypertensive rats receiving clonidine," Liver, 1994, 14: 45-49.*
Deans et al., "Novel therapies for sepsis: a review," 58 *J Trauma* 867 (2005).
Dellinger et al., "Surviving sepsis campaign : international guidelines for management of severe sepsis and septic shock: 2008," 34 *Int Care Med* 17 (2008).
Sprung et al., "Hydrocortisone therapy for patients with septic shock," 358 *N Engl J.Med* 111 (2008).
Benedict et al., "Arterial norepinephrine changes in patients with septic shock," 38 *Circ Shock* 165 (1992).
Collin et al., "Pathophysiological mechanisms of vascular hyporesponsiveness in shock states," 17 *Reanimation* 101 (2008).
Petros et al., "Effect of nitric oxide synthase inhibitors on hypotension in patients with septic shock," 338 *Lancet* 1557 (1991).
Rivers et al., "Early goal directed therapy in the treatment of severe sepsis and septic shock," 345 *N Engl J Med* 1368 (2001).
Putensen et al., "Long-term effects of spontaneous breathing during ventilatory support in patients with acute lung injury," 164 *Am J Respir Crit Care Med* 43 (2001).
Schultz et al., "Alpha 2- and beta 2-adrenoceptor downregulation in marathon runners," 7 *J Hypertens (Suppl)* S48 (1989).
Butler et al., "Beta-adrenoceptor adaptation to acute exercise," 344 *J Physiol (Lond)* 113 (1983).
Ohman et al., "Beta-adrenoceptor adaptation to endurance training," 10 *J Cardiovasc Pharmacol* 728 (1987).
Mathias et al., "Antihypertensive effects of clonidine in tetraplegic subjects devoid of central sympathetic control," 57 *Clin Sci* 425S (1979).
Robertson et al., "Clonidine raises blood pressure in severe idiopathic orthostatic hypotension," 74 *Am J Med* 193 (1983).
Bannister et al., "β-Receptor numbers and thermodynamics in denervation supersensitivity," 319 *J Physiol* 369 (1981).
Dollery et al., "Haemodynamic studies with methyldopa : effect on cardiac output and response to pressor amines," 25 *Br Heart J* 670 (1963).
Burn et al., "The action of sympathomimetic amines in animals treated with reserpine," 144 *J Physiol* 314 (1958).
Pichot et al., "Increased Pressor Response to Noradrenaline During Septic Shock Following Clonidine?," 38 *Anesthesia and Intensive Care* 784 (Jul. 2010).
Freed et al., "Changes in brain alpha-adrenergic receptors after alphamethyldopa administration to spontaneously hypertensive rats," 6 *Hypertension (Suppl. II)* 11-34 (1984).
Kobinger et al., "The central modulatory effect of clonidine on the cardiodepressor reflex after suppression of synthesis and storage of noradrenaline," 30 *Eur J Pharmacol* 56 (1975).
Quintin et al., "Clonidine for major vascular surgery in hypertensive patients : a double blind controlled randomized study," 83 *Anesth Analg* 687 (1996).
Zoukos et al., "Up-regulation of β-adrenoceptors on circulating mononuclear cells after reduction of central sympathetic outflow by clonidine in normal subjects," 2 *Clin Auton Res* 165 (1992).
Nishikawa et al., "Oral clonidine preanesthetic medication augments the pressor responses to intravenous ephedrine in awake or anesthetized patients," 74 *Anesthesiology* 705 (1991).
Inomata et al., "Enhancement of pressor response to intravenous phenylephrine following oral clonidine medication in awake and anaesthetized patients," 42 *Can J Anaesth* 119 (1995).
Parlow et al., "The effects of clonidine on sensitivity to phenylephrine and nitroprusside in patients with essential hypertension recovering from surgery," 88 *Anesth Analg* 1239 (1999).
De Kock et al., "The effects of intraoperative intravenous clonidine on fluid requirements, hemodynamic variables, and support during liver transplantation : a prospective, randomized study," 86 *Anesth Analg* 468 (1998).

(Continued)

*Primary Examiner* — Julia Ha
(74) *Attorney, Agent, or Firm* — McAndrews, Held & Malloy Ltd.

(57) ABSTRACT

Provided herein are methods and compositions for treating septic hypotension. More specifically, the methods may comprise, administering one alpha-2 agonist or other sympatholytic and at least one vasopressor.

8 Claims, No Drawings

(56) References Cited

PUBLICATIONS

Morris et al., "Cross-regulation between G-protein-coupled receptors. Activation of beta 2-adrenergic receptors increases alpha 1-adrenergic receptor mRNA levels," 266 *J Biol Chem* 2233 (991).

Copik et al., "Facilitatory interplay in alpha 1a and beta 2 adrenoceptor function reveals a non-Gq signaling mode: implications for diversification of intracellular signal transduction," 75 *Mol Pharmacol* 713 (2009).

Silverman et al., "Impaired beta-adrenergic receptor stimulation of cyclic adenosine monophosphate in human septic shock: association with myocardial hyporesponsiveness to catecholamines," 21 *Crit Care Med* 31 (1993).

Saito et al., "Corticosteroid effect on early beta-adrenergic down-regulation during circulatory shock: hemodynamic study and beta-adrenergic receptor assay," 21 *Intensive Care Med* 204 (1995).

Grimm et al., "Chronic reserpine administration selectively up-regulates beta 1- and alpha 1b-adrenergic receptors in rat brain: an autoradiographic study," 47 *Neuroscience* 77 (1992).

Ellis et al., Effect of a maldistribution of microvascular blood flow on capillary O2 extraction in sepsis, 282 *Am J Physio Heart Circ. Physioll* H156 (2002).

Dodd-o et al., Preserved sympathetic response to hypotension despite perioperative alpha-2 agonist administration, 84 *Anesth Analg* 1208 (1997).

Sauder et al., "Sedation and analgesia in intensive care," 27 *Ann Fr Anesth Reanim* 541 (2008).

Hofer et al., "Central Sympatholytics Prolong Survival in Experimental Sepsis," 13 *Critical Care* R11 (2009).

Thomas et al., Administration of Angiotensin II in Refractory Septic Shock, 19 *Critical Care Medicine* 1084 (1991).

Spronk et al., "Nitroglycerin in septic shock after intravascular volume resuscitation," 360 *Lancet* 1395 (2002).

Mangano et al., Effect of Atenolol on Mortality and Cardiovascular Morbidity After Noncardiac Surgery, 335 *N Eng J Med* 1713 (1996).

Wallace et al., "Effect of Clonidine on Cardiovascular Morbidity and Mortality After Noncardiac Surgery," 101 *Anesthesiology* 284 (2004).

Schmittinger et al., "How to Protect the Heart in Septic Shock: A Hypothesis on the Pathophysiology and Treatment of Septic Heart Failure," 74 *Medical Hypotheses* 460 (2010).

Myburgh, "An Appraisal of Selection and Use of Catecholamines in Septic Shock—Old Becomes New Again," 8 *Critical Care and Resuscitation* 353 (2006).

Taniguchi et al., "Effects of Dexmedetomidine on Mortality Rate and Inflammatory Responses to Endotoxin-induced Shock in Rats," 32 *Critical Care Med* 1322 (2004).

Taniguchi et al., "Dose- and Time-related Effects of Dexmedetomidine on Mortality Rate and Inflammatory Responses to Endotoxin-induced Shock in Rats," 22 *J.Anesth* 221 (2008).

\* cited by examiner

METHOD AND DRUG COMPOSITION FOR TREATING SEPTIC SHOCK HYPOTENSION

INTRODUCTION

Septic shock bears a high mortality ranging from 30 to 70%. This amounts to an estimated toll of 210,000 deaths per year in the USA.[1] Septic shock is defined as a systolic blood pressure (SBP)<90 mm Hg despite adequate volume loading[2] or vasopressors for more than 1 h.[3] A key problem encountered upon septic shock is a low vascular reactivity: vasopressors (noradrenaline [NA], rarely adrenaline [A] or vasopressin [AVP]) hardly succeed in restoring BP even if low normal pressure (e.g. ≥65 mm Hg) is accepted. More puzzling, this low response to exogenous vasopressors occurs despite high endogenous catecholamines concentrations: the higher the concentrations, the higher the mortality.[4]

Attempts to restore vascular reactivity (NO inhibitors, low dose steroids) have met with little success. Low vascular reactivity may lead to refractory shock and death. Low vascular reactivity may be linked to desensitization or down regulation of alpha-1 adrenergic receptors. Vascular reactivity is primarily based upon vasopressor requirements. Vascular reactivity may also be assessed more rigorously using the response to graded infusions of vasopressors or to bolus injection of increasing doses of vasopressors (alpha-1 agonist, phenylphrine [PE]; NA: 1, 2, 4, 8, 10 . . . μg of bolus NA): the measured increments in pressure allows one to calculate a pressor dose 20 mm Hg (PD20) and determine the vascular reactivity. To explain for this low reactivity, desensitization or down-regulation of alpha-1 and beta-1 adrenergic receptors is called upon. Desensitization of beta-adrenergic receptors in septic shock has been studied (see below). By contrast, alpha-1 receptors have been poorly studied with respect to shock.[5] Attempts have been made to obviate reduced vascular reactivity, using nitric oxide (NO) inhibition,[6] methylene blue[7] or low dose steroids.[8]

Septic shock is followed by massive release of noradrenaline. Plasma NA concentrations are higher by a factor 2 in non-survivors following septic shock, as compared to survivors (mean: survivors: 1960 pg.ml−1; non-survivors: 4360 pg.ml−1). Furthermore, head-up tilt increased plasma NA in survivors, but failed to do so in non-survivors.[4]

BRIEF DESCRIPTION OF THE INVENTION

One of the purposes of the invention is to solve the following problem: the poor responsiveness, or reduced vascular reactivity, to exogenous vasopressors used to rise the blood pressure (BP) to fight against septic shock.

The inventors hypothesize that alpha-1 receptors undergo desensitization or down regulation upon septic shock as a consequence of massive sympathetic activation and release of endogenous NA and adrenaline release. If sympathetic hyperactivity is blunted by any sympathetic inhibitor or centrally acting antihypertensive agent (alpha-2 agonists: clonidine, dexmedetomidine, etc.; imidazoline antagonist: rilmelidine, monoxidine, etc.; alpha-methydopa, alpha-methylparatyrosine, etc.), the release of endogenous catecholamines upon septic shock will be reduced if an alpha-2 agonist is administered together with the state of the art treatment (state of the art treatment refers to Dellinger et al).[2] Therefore, the desensitization or down regulation of alpha-1 receptors and associated reduced vascular reactivity will be partly or entirely blunted: a near normal response to exogenous vasopressors will be restored more quickly in patients treated with a combination of alpha-2 agonists and state of the art treatment as compared with patients treated with the state of the art treatment alone.

Thus the invention pertains to:
1. a method for treating septic shock hypotension consisting in administering to the patient alpha-2 agonists (e.g. clonidine or dexmedetomidine) or other sympatholytics (rilmelidine, monoxidine, alpha-methyldopa, alpha-methylparatyrosine) upon septic shock in combination of at least one vasopressor (e.g. NA), and state of the art volume load.[2,9] The volume load is based on echocardiographic or hemodynamic assessment.

2. a drug composition for treating septic shock hypotension including alpha-2 agonists (e.g. clonidine or dexmedetomidine) or other sympatholytics (rilmelidine, monoxidine, alpha-methyldopa, alpha-methylparatyrosine) upon septic shock and a vasopressor.

The use of the means according to the invention will lead to a reduction in vasopressor requirements needed to restore adequate BP. This counter-intuitive proposal is based on the hypothesis that alpha-2 agonists administration will reduce the massive release of endogenous catecholamines. Reduced plasma endogenous catecholamines concentrations will be followed by a reduced de-sensitization or a reduced down regulation of alpha-1 receptors. Therefore, a gradual re-sensitization of alpha-1 adrenergic receptors will occur. In turn, this will lead to lowered vasopressor requirement, with respect to dose and duration. Our hypothesis, based on a reverse "denervation hypersensitivity", is at variance with the accepted view, which rests only on volume load and vasopressors and emphasizes restoration of blood pressure per se. Several observations in the cardiology and anesthesia setting support increased vascular reactivity following alpha-2 agonist administration. Our preliminary observations in the setting of septic shock demonstrated again such an increased vascular reactivity. Improved outcome was also observed. Rigorous work is warranted to verify reduced vasopressor requirement and improved outcome, when alpha-2 agonist is associated with the state of the art treatment of septic shock. This state of the art treatment includes generous volume load[9] combined to vasopressors to maintain perfusion pressure (usually mean BP>65 mm Hg or to adequate diuresis).[2] Indeed, alpha-2 adrenergic receptors exert in the synaptic cleft a negative feed-back control on noradrenaline release from adrenergic/noradrenergic neurons and from peripheral sympathetic nerve endings. Given the lower intrasynaptic catecholamines concentrations, the alpha-1 desensitization will be reduced: a gradual re-sensitization will occur. Then, vascular reactivity to exogenously administered vasopressors will be restored much more quickly if sympathetic inhibitors are administered in addition to state of the art treatment,[2] as opposed to the state of the art treatment alone. Even if the vascular reactivity in patients presenting with septic shock and treated with combined state of the art and alpha-2 agonist (administered e.g as clonidine 1 μg.kg−1.h−1 as a slow infusion over 24 h without loading dose) remain lowered as compared to age-matched healthy volunteers, in alpha-2 agonist treated patients, this vascular reactivity will return earlier toward pre-septic shock values, after alpha-2 agonist administration.

Caveats: For simplicity, this discussion will be restricted: a) a degree of compartmentalization of endogenous vs. exogenously administered catecholamines is implied: intravascular exogenous NA may not freely access to the synaptic cleft. b) this hypothesis is primarily concerned with alpha-1 receptors but may hold true with respect to beta-receptors. Indeed, myocardial dysfunction[10] (reduced left ventricle [LV] systolic or diastolic function, right ventricle dilatation) may occur during septic shock. c) this hypothesis may hold true also in other syndromes in which a massive release of endogenous catecholamines combines with desensitization of adrenergic receptors (status asthmaticus, refractory cardiogenic shock, prolonged haemorrhagic shock after adequate volume compensation, refractory anaphylactic shock, etc.). Refractory shock means here a shock state not or poorly responding to high dose noadrenaline/adrenaline/dobutamine infusion, after appropriate echocardiographic or hemodynamic assessment. d) that alpha-2 agonists allow for both sedation and spontaneous ventilation combined to mechanical ventilation (non-invasive or invasive) will not be further considered. Obviously, maintenance of spontaneous ventilation allows for improved cardio-ventilatory interactions.[11]

EXAMPLES

To treat severe hypotension with an alpha-2 agonist administered in addition to the state of the art treatment can hardly be more counter-intuitive.

Down-regulation of adrenergic receptors: In sevoflurane-anesthetized rats submitted to sepsis (lipopolysaccharide), the blood pressure response to NA (i.e. vascular reactivity) was reduced by a factor 5, as compared to control animals. Accordingly, the mRNAs of alpha-1 receptors were much lowered, irrespective of the organ considered (heart, aorta, lung, kidney, liver).[12] A down regulation of beta-receptors (decrease in the density of beta receptors on lymphocytes, unchanged isoproterenol stimulated cyclicAMP [cAMP] production) is observed following short term exercise (10 min, 90% of maximal HR).[13] A long distance race is associated with a decrease in beta receptors density and unchanged affinity for a beta-blocker (alprenolol).[14] Following a marathon, this observation holds true also for alpha-2 receptors.[15] In patients presenting with septic shock and a 76% mortality, the accumulation of cAMP following isoproterenol challenges was lowered, as compared to septic patients or volunteers. Furthermore challenges with a beta-agonist, dobutamine, led to virtually no changes in heart rate (HR) in septic shock patients as compared to septic patients (septic shock patients: +3 bpmin following 10 µg.kg−1.min−1; septic patients: +12 bpmin). A post hoc analysis reveals no difference with respect to beta receptor dysfunction when patients receiving low dose catecholamines are opposed to patients receiving high dose catecholamines.[16] Patients having received catecholamines infusion for more than 72 h presented a lower beta-receptor myocardial density as opposed to patients having received no catecholamines.[17] Taken together, these data show a down-regulation of adrenergic receptors upon massive release of endogenous catecholamines.

Up-regulation: In tetraplegic patients, clonidine does not lower BP nor plasma catecholamines concentrations. Neither does clonidine modify the pressor response to noradrenaline or phenylephrine[18]. By contrast, in patients presenting with severe idiopathic hypotension, under baseline conditions a) the dose of tyramine needed to increase BP was twice as high as in normal subject. b) the dose of phenylephrine needed to increase BP was much reduced in patients with idiopathic hypertension as compared to normal subjects. c) clonidine 0.4-0.8 mg p.o. increases the SBP by 40-70 mm Hg.[19] An up-regulation of alpha-1 receptors possibly occurs in patients with idiopathic hypotension, given a depletion of noradrenaline stores. This alpha-1 up-regulation may be further enhanced when clonidine is administered.

Upon Shy-Drager syndrome (multiple system atrophy), "denervation supersensitivity" is accompanied by a 6 fold increase in beta receptors, with no change in affinity as compared to healthy volunteers.[20] However chronotropic response to isoproterenol infusion was increased in Shy Drager patients.[20] In hypertensive patients, alpha-methyldopa leads to an increase in the pressor response to NA with a prolonged duration of the pressor response.[21] In animals, reserpine which depletes noradrenaline stores a) enhances the pressor response to NA and phenylphrine (PE).[22] b) increases the beta-1 and alpha1b-receptors binding in selected areas of the central nervous system.[23] Alpha-methyldopa administration (72 h) leads to central up-regulation of alpha-1 receptors and down regulation of alpha-2 receptors. The phenomenon is accentuated is hypertensive rats as compared to normotensive controls.[24] Finally, in decerebrated rats depleted from catecholamines by reserpine and alpha-methylparatyrosine, clonidine "considerably" elevates the resting BP.[25]

Clonidine (2 µg.kg−1.h−1 i.v. over 10 min) in healthy volunteers induced after 30 to 60 min an increase of beta receptors density located on lymphocytes, with a decrease in affinity. No difference was observed in vitro. Following reduction in sympathetic nervous activity and plasma catecholamines concentrations, a rapid externalisation of beta receptors was postulated, leading to increased density and decreased affinity.[26] In hypertensive patients, clonidine (0.2-0.4 mg/day for 6-8 weeks) increased the sensitivity to phenylephrine (pressor dose to increase BP by 20 mm Hg: PD20: 96 µg to 39 µg, n=30, p<0.05) and the chronotropic response to isoproterenol (chronotropic dose to increase HR by 25 bpmin: CD25: 2.6 µg to 1.9, ns). Accordingly in healthy patients (ASA1) a) the response to ephedrine in conscious or anesthetized patients is increased following clonidine (5 µg.kg−1 p.o). The pressor response is enhanced to a greater extent in anesthetized patients[27]: this result may be explained by a lowering of plasma catecholamines concentration by anesthesia in the anesthetized patient as opposed to the conscious patient. Such a lowered plasma catecholamines concentration under anesthesia after clonidine administration would exaggerate a "denervation hypersensitivity", when compared to the conscious baseline state. b) the pressor response to phenylpehrine is increased in awake and anesthetized patients after clonidine administration (control: +17 mm Hg above baseline SBP; clonidine: +31 mm Hg, in response to a phenylephrine bolus 2 µg.kg−1).[28] Furthermore, following clonidine administration, a) the chronotropic reactivity to isoproterenol is increased in the setting of aortic surgery.[29] b) the vascular reactivity to phenylephrine is increased in the setting of major abdominal surgery.[30] In the setting of liver transplant, clonidine administration is associated with lowered noradrenaline requirements.[31] More intriguing, despite this lowered requirement for NA, the nadir of systolic and diastolic pressure upon liver declamping is higher in the clonidine group as referred to the placebo group: presumably, a lower sympathetic activity is associated with a less vasoplegia and a better preserved vasomotor tone. This implies that other factors are more important than sympathetic activity to regulate pressure in the setting of major surgery i.e. outside the setting of septic shock. Taken together, these data show an increase vascular reactivity when endogenous catecholamines release is decreased.

Cross regulation between alpha and beta adrenergic receptors: An interaction between adrenergic receptors has been considered as an in vivo only consequence of changes in endogenous catecholamines concentrations occurring upon septic shock. However, in vitro an interaction may exist: a) in vitro, adrenaline evokes a short term (2-8 h) increases in alpha-1 messengerRNA (mRNA). A beta-2 antagonist, propranolol, suppresses this increases in alpha-1 mRNA, but do not affect the decrease in alpha-1 binding. By contrast, an alpha-1 antagonist, phentolamine, evoked an inverse pattern: unaffected increase in alpha-1 mRNA, but suppressed decrease in alpha-1 binding. Early cross regulation occurs at mRNA level. By contrast delayed down regulation of binding occurs via agonist activation at alpha-1 receptors.[32] b) NA or a selective alpha-1A agonist (A61103) do not increase intracellular calcium unless beta-2 adrenergic receptor is activated by isoproterenol.[33] Therefore, some interplay may occur between alpha and beta receptors (e.g. alpha-1 vs. beta vs. alpha-2) within the membrane itself. Can this in vitro scenario apply to the clinical setting?

Improved peripheral blood flow: In rats, a maldistribution of $O_2$ supply occurs: some areas are oversupplied, while other areas are undersupplied: the decrease in $O_2$ supply is not uniform but patchy with areas of stopped flow capillaries, with decreased venular-end capillary saturation in $O_2$, and areas of fast flow capillaries.[34] In patients presenting with moderate septic shock (mean BP>60 mm Hg, central venous pressure>12 mm Hg, impaired capillary refill), nitroglycerin bolus (0.5 mg) followed by nitroglycerin infusion (2 mg.h−1; range: 0.5-4 mg.h−1) was added to state of the art management. 7 out of 8 patients were discharged alive. Peripheral blood flow improved.[35] Turning to alpha-2 agonists, could our preliminary results obtained with clonidine (see below) be linked to reduced microvascular arterio-venous shunting, improved microvascular flow, and/or reduced acidosis rather than an interplay between alpha-2 and alpha-1 receptors?

Clinical observations: From the observation of a possible up-regulation of alpha-1 and beta-1 receptors upon recovery from aortic or abdominal surgery[29, 30] to the present hypothesis (upregulation of alpha-1 receptors upon septic shock treated by the state of the art therapy associated with an alpha-2 agonist), a series of observations were needed: a) we observed many occurrences of septic shock in surgical patients pre-treated with clonidine. Recovery was uneventful, linked apparently more to the swiftness of surgery and the quality of the critical care management, but unimpaired by clonidine administration. The response to vasopressors and inotropic agents was not blunted. Moreover, upon shock, the patients presented a low BP without any peripheral mottling: a very good capillary refill was observed despite low BP. b) preserved sympathetic re-activity was observed upon septic shock in a patient pre-treated with clonidine. With plasma clonidine concentrations in the therapeutic range (1-2 ng.ml−1), a 5-10 fold rise in plasma catecholamines concentrations was observed.[36] Unfortunately, the patient was not challenged with boluses of vasopressor or inotrope. c) patients already present in a critical care unit and sedated with clonidine (1-2 μg.kg−1.h−1 (37)) presented septic shock. They were successfully resuscitated using the state of the art management.[2] Again, the use of vasopressors Or inotropes was not impaired. In these patients, formal challenges were undertaken with noradrenaline or dobutamine boluses to rise the SBP by 25 mm Hg or the HR by 20 bpmin, respectively. Initially, immediately completion of the initial resuscitation (volume, steroids, NA),[2, 9] the vascular response to these drugs was very low. This is compatible with a low vascular and chronotropic reactivity upon septic shock (see above). By contrast, within 24 h of state of the art treatment combined to clonidine infusion (1 μg.kg−1.h−1 for 24 h), the bolus dose of NA required to increase the SBP by 25 mm Hg was lowered by 50 to 75%, as compared to the baseline reactivity observed upon completion of initial resuscitation (Quintin, unpublished data). In addition, the NA requirements needed to support the BP to an acceptable level (MAP>65 mm Hg or to an adequate diuresis) were reduced dramatically over 24 h. Total withdrawal of NA infusion occurred within 48-72 h, with acceptable diuresis and SBP. Finally, more rapid reduction in lactate plasma concentration together with faster improvement of superior vena cava oxygen saturation were observed when clonidine was administered to patients presenting with septic shock and treated according to the state of the art, as opposed to patients treated only with the state of the art. Taken together, the clinical course was transformed by the use of an alpha-2 agonist in addition to the state of the art.

Clinical trial: We have superimposed an alpha-2 agonist vs. placebo in addition to the state of the art management of septic shock[2, 9] and observe a) the vascular and chronotropic reactivity (response to increasing boluses of e.g. NA and dobutamine) at various time intervals (e.g. immediately after completion of initial treatment then e.g. every 24 h up to withdrawal of vasopressor or inotrope infusions) b) the requirements for infusions of vasopressors and inotropes to achieve an acceptable MAP (e.g.>65 mm Hg) with an acceptable diuresis c) the duration of exposure to vasopressors and inotropes clinically required d) the markers commonly viewed as indices of peripheral oxygen utilization (e.g. lactates, mixed venous or superior vena cava $O_2$ saturation) e) the morbidity and mortality.

The results are the following for the patients presenting with septic shock (SBP<90 mm Hg despite adequate volume loading or vasopressors for more than 1 h) and treated with an alpha-2 agonist superimposed on the state of the art treatment: a) upon inclusion following initial resuscitation identical vascular reactivity upon challenge with increasing doses of e.g. noradrenaline and dobutamine b) increased vascular reactivity after 24 h in the patients treated with an alpha-2 agonist. c) reduced requirements for vasopressor and inotropes both with respect to dosage and duration of infusion d) reduced lactates concentration together with increased mixed (or superior vena cava) venous oxygen saturation d) improved morbidity and mortality (reduced duration of invasive or non-invasive ventilation, reduced incidence of acute renal and liver failure, reduced length of stay in critical care unit and hospital) and reduced short- and long-term mortality. Given the 30-70% mortality associated with septic shock, this invention warrants consideration.

As de-sensitization or down regulation of adrenergic receptors occur also upon status asthmaticus, cardiogenic shock (following myocardial infarction or admission to the medical coronary care unit for any medical reason or following cardiac surgery with or without cardiopulmonary bypass, with or without placement of intraaortic ballon pump or placement of left ventricular assist device), terminal hemorrhagic shock (after adequate correction of volume), refractory anaphylactic shock, malignant hyperthermia, this therapeutic schema will also be of benefit in these various indications with similar means (state of the art treatment and alpha-2 agonists administration without bolus). Vasopressor administration upon status asthmaticus may not be needed, except immediately upon tracheal intubation and mechanical reventilation. Permissive hypercapnia has largely reduced the need for vasopressors in the setting of status asthmaticus.

The possibility of using mechanical ventilation in intubated patients under spontaneous ventilation (pressure support ventilation, airway pressure release ventilation, etc.) is considered, given its potential beneficial effects, but not delineated any further, as this patent focuses on circulation.

1. Deans K J, Haley M, Natanson C, Eichacker P Q, Minneci P C. Novel therapies for sepsis: a review. J Trauma 2005; 58:867-74

2. Dellinger R P, Levy M M, Carlet J M, Bion J, Parker M M, Jaeschke R, Reinhart K, Angus D C, Brun-Buisson C, Beale R, Calandra T, Dhainaut J F, Gerlach H, Harvey, Marini J J, Marshall J, Ranieri M, Ramsay G, Sevransky J, Thompson B T, Townsend S, Vender J S, Zimmermann J L, Vincent J L. Surviving sepsis campaign: international guidelines for management of severe sepsis and septic shock: 2008. Int Care Med 2008; 34:17-60

3. Sprung C L, Annane D, Keh D, Moreno R, Singer M, Freivogel K, Weiss Y G, Benbenishty J, Kalenka A, Forst H, Laterre P F, Reinhart K, Cuthbertson B H, Payen D, Briegel J. Hydrocortisone therapy for patients with septic shock. N Engl J Med 2008; 358:111-24

4. Benedict C R, Rose J A. Arterial norepinephrine changes in patients with septic shock. Circ Shock 1992; 38:165-72

5. Collin S, Levy B. Pathophysiological mechanisms of vascular hyporesponsiveness in shock states. Reanimation 2008; 17:101-10

6. Petros A, Bennett D, Valiance P. Effect of nitric oxide synthase inhibitors on hypotension in patients with septic shock. Lancet 1991; 338:1557-8

7. Schneider F, Lutun P, Hasselmann M, Stoclet J C, Tempe J D. Methylene blue increases systemic vascular resistance in human septic shock. Preliminary observations. Intensive Care Med 1992; 18:309-11

8. Bellissant E, Annane D. Effect of hydrocortisone on phenylephrine—mean arterial pressure dose-response relationship in septic shock. Clin Pharmacol Ther 2000; 68:293-303

9. Rivers E, Nguyen B, Haystad S, Ressler J, Muzzin A, Knoblich B, Peterson E, Tomlanovich M. Early goal directed therapy in the treatment of severe sepsis and septic shock. N Engl J Med 2001; 345:1368-77

10. Parker M M, Shelhamer J H, Bacharach S L, Green M V, Natanson C, Frederick T M, Damske B A, Parrillo J E. Profound but reversible myocardial depression in patients with septic shock. Ann Intern Med 1984; 100:483-90

11. Putensen C, Zech S, Wrigge H, Zinserling J, Stuber F, von ST, Mutz N. Long-term effects of spontaneous breathing during ventilatory support in patients with acute lung injury. Am J Respir Crit Care Med 2001; 164:43-9

12. Bucher M, Kees F, Taeger K, Kurtz A. Cytokines down-regulate alpha1-adrenergic receptor expression during endotoxemia. Crit Care Med 2003; 31:566-71

13. Butler J, Kelly J G, O'Malley O, Pidgeon F. Beta-adrenoceptor adaptation to acute exercise. J Physiol (Lond) 1983; 344:113-7

14. Ohman E M, Butler J, Kelly J, Horgan J, O'Malley K. Beta-adrenoceptor adaptation to endurance training. J Cardiovasc Pharmacol 1987; 10:728-31

15. Schultz K D, Fritschka E, Kribben A, Rothschild M, Thiede H M, Distler A, Philipp T. Alpha 2- and beta 2-adrenoceptor downregulation in marathon runners. J Hypertens Suppl 1989; 7:S48-S49

16. Silverman H J, Penaranda R, Orens J B, Lee N H. Impaired beta-adrenergic receptor stimulation of cyclic adenosine monophosphate in human septic shock: association with myocardial hyporesponsiveness to catecholamines. Crit Care Med 1993; 21:31-9

17. Saito T, Takanashi M, Gallagher E, Fuse A, Suzaki S, Inagaki O, Yamada K, Ogawa R. Corticosteroid effect on early beta-adrenergic down-regulation during circulatory shock: hemodynamic study and beta-adrenergic receptor assay. Intensive Care Med 1995; 21:204-10

18. Mathias C J, Reid J L, Wing L M H, Frankel H L, Christensen N J. Antihypertensive effects of clonidine in tetraplegic subjects devoid of central sympathetic control. Clin Sci 1979; 57:425S-8S 19. Robertson D, Goldberg M R, Hollister A S, Wade D, Robertson R M. Clonidine raises blood pressure in severe idiopathic orthostatic hypotension. Am J Med 1983; 74:193-200

20. Bannister R, Boylston A W, Davies I B, Mathias C J, Sever P S, Sudera D. beta-Receptor numbers and thermodynamics in denervation supersensitivity. J Physiol 1981; 319:369-77

21. Dollery C T, Harington M, Hodge J V. Haemodynamic studies with methyldopa: effect on cardiac output and response to pressor amines. Br Heart J 1963; 25:670-6

22. Burn J H, Rand M J. The action of sympathomimetic amines in animals treated with reserpine. J Physiol 1958; 144:314-36

23. Grimm L J, Blendy J A, Kellar K J, Perry D C. Chronic reserpine administration selectively up-regulates beta 1- and alpha 1b-adrenergic receptors in rat brain: an autoradiographic study. Neuroscience 1992; 47:77-86

24. Freed C R, Wang C H, U'Prichard DC. Changes in brain alpha-adrenergic receptors after alphamethyldopa administration to spontaneously hypertensive rats. Hypertension 1984; 6:ll34-ll39

25. Kobinger W, Pichler L. The central modulatory effect of clonidine on the cardiodepressor reflex after suppression of synthesis and storage of noradrenaline. Eur J Pharmacol 1975; 30:56-62

26. Zoukos Y, Thomaides T, Pavitt D V, Leonard J P, Cuzner M L, Mathias C J. Upregulation of beta adrenoceptors on circulating mononuclear cells after reduction of central sympathetic outflow by clonidine in normal subjects. Clin Auton Res 1992; 2:165-70

27. Nishikawa T, Kimura T, Taguchi N, Dohi S. Oral clonidine preanesthetic medication augments the pressor responses to intravenous ephedrine in awake or anesthetized patients. Anesthesiology 1991; 74:705-10

28. Inomata S, Nishikawa T, Kihara S, Akiyoshi Y. Enhancement of pressor response to intravenous phenylephrine following oral clonidine medication in awake and anaesthetized patients. Can J Anaesth 1995; 42:119-25

29. Quintin L, Bouilloc X, Butin E, Bayon M C, Brudon J R, Levron J C, Tassan T, Boucaud C, Tissot S, Frehring B, Petit P, Danays T, Viale J P, Ghignone M. Clonidine for aortic surgery in hypertensive patients: a double blind controlled randomized study. Anesth Analg 1996; 83:687-95

30. Parlow J, Sagnard P, Begou G, Viale J P, Quintin L. The effects of clonidine on sensitivity to phenylephrine and nitroprusside in patients with essential hypertension recovering from surgery. Anesth Analg 1999; 88:1239-43

31. De Kock M, Laterre P F, Van Obbergh L, Carlier M, Lerut J. The effects of intraoperative intravenous clonidine on fluid requirements, hemodynamic variables, and support during liver transplantation: a prospective, randomized study. Anesth Analg 1998; 86:468-76

32. Morris G M, Hadcock J R, Malbon C C. Cross-regulation between G-protein-coupled receptors. Activation of beta 2-adrenergic receptors increases alpha 1-adrenergic receptor mRNA levels. J Biol Chem 1991; 266:2233-8

33. Copik A J, Ma C, Kosaka A, Sandeo S, Trane A, Ho H, Dietrich P S, Yu H, Ford A P, Button D, Milla M E. Facilitatory interplay in alpha 1a and beta 2 adrenoceptor function reveals a non-Gq signaling mode: implications for diversification of intracellular signal transduction. Mol Pharmacol 2009; 75:713-28

34. Ellis C G, Bateman R M, Sharpe M D, Sibbald W J, Gill R. Effect of a maldistribution of microvascular blood flow on capillary O2 extraction in sepsis. Am J Physiol 2002; 282: H156-H164

35. Spronk P E, Ince C, Gardien M J, Mathura K R, Oudemans-van Straaten H M, Zandstra D F. Nitroglycerin in septic shock after intravascular volume resuscitation. Lancet 2002; 360:1395-6

36. Dodd-o J M, Breslow M J, Dorman T, Rosenfeld B A. Preserved sympathetic response to hypotension despite perioperative alpha-2 agonist administration. Anesth Analg 1997; 84:1208-10

37. Sauder P, Andreoletti M, Cambonie G, Capellier G, Feissel M, Gall O, Goldran-Toledano D, Kierzek G, Mateo J, Mentec H, Mion G, Rigaud J P, Seguin P. Sedation and analgesia in intensive care. French Critical Care Society. Ann Fr Anesth Reanim 2008; 27:541-51

The invention claimed is:

1. A method for treating septic hypotension in a patient suffering from septic shock, comprising administering to said patient at least one alpha-2 agonist selected from the group consisting of clonidine or dexmedetomidine or sympatholytic selected from the group consisting of rilmelidine, monoxidine, alpha-methyldopa and alpha-methylparatyrosine, and at least one catecholamine vasopressor selected from the group consisting of noradrenaline, adrenaline, and phenylephrine.

2. The method of claim 1, wherein said alpha-2 agonist is clonidine.

3. The method of claim 1, wherein said vasopressor comprises noradrenaline.

4. The method of claim 2, wherein said administration of clonidine comprises administering an amount of clonidine ranging from 0.5-4 µg/kg/h without bolus administration.

5. The method of claim 4, comprises administering clonidine in an amount of 1 µg/kg/h without bolus administration.

6. The method of claim 1, wherein said administration comprises administering dexmedetomidine in an amount ranging from 0.25-2 µg/kg/h without bolus administration.

7. The method of claim 1, wherein said method comprises administering said alpha-2 agonist via intravenous infusion.

8. The method of claim 1, wherein said alpha-2 agonist is dexmedetomidine.

* * * * *